United States Patent
Lai et al.

(10) Patent No.: US 7,217,125 B2
(45) Date of Patent: *May 15, 2007

(54) SELF-LIGATING ORTHODONTIC APPLIANCE WITH CLIP

(75) Inventors: Ming-Lai Lai, Arcadia, CA (US); Jirina V. Pospisil, Hacienda Heights, CA (US); Hoang V. Nguyen, Garden Grove, CA (US); Joyce C. Ho, Temple City, CA (US)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/317,346

(22) Filed: Dec. 23, 2005

(65) Prior Publication Data

US 2006/0147868 A1    Jul. 6, 2006

Related U.S. Application Data

(63) Continuation-in-part of application No. 10/900,779, filed on Jul. 28, 2004, now abandoned.

(51) Int. Cl.
*A61C 3/00* (2006.01)
(52) U.S. Cl. ...................................................... 433/11
(58) Field of Classification Search .............. 433/8–11, 433/13–14, 22
See application file for complete search history.

(56) References Cited

U.S. PATENT DOCUMENTS

| 1,991,047 | A |   | 2/1935  | Boyd et al. |
| 3,327,393 | A |   | 6/1967  | Brader |
| 3,724,074 | A |   | 4/1973  | Wallshein |
| 4,103,423 | A |   | 8/1978  | Kessel |
| 4,171,568 | A |   | 10/1979 | Forster |
| 4,527,975 | A | * | 7/1985  | Ghafari et al. ................. 433/8 |
| 4,551,094 | A |   | 11/1985 | Kesling |
| 4,712,999 | A |   | 12/1987 | Rosenberg |
| 5,269,681 | A |   | 12/1993 | Degnan |
| 5,358,402 | A |   | 10/1994 | Reed et al. |
| 5,366,372 | A |   | 11/1994 | Hansen et al. |
| 5,380,196 | A |   | 1/1995  | Kelly et al. |
| 5,439,379 | A |   | 8/1995  | Hansen |
| 5,474,445 | A |   | 12/1995 | Voudouris |
| 5,516,284 | A |   | 5/1996  | Wildman |
| 5,630,715 | A |   | 5/1997  | Voudouris |
| 5,685,711 | A |   | 11/1997 | Hanson |
| 5,711,666 | A |   | 1/1998  | Hanson |
| 5,857,850 | A |   | 1/1999  | Voudouris |
| 5,863,199 | A |   | 1/1999  | Wildman |
| 6,302,688 | B1 |  | 10/2001 | Jordan et al. |
| 6,325,622 | B1 |  | 12/2001 | Kelly et al. |
| 6,582,226 | B2 |  | 6/2003  | Jordan et al. |
| 2004/0086825 | A1 | | 5/2004 | Lai et al. |
| 2004/0086826 | A1 | | 5/2004 | Pospisil |
| 2005/0095549 | A1 | | 5/2005 | Cinader et al. |
| 2005/0123875 | A1 | | 6/2005 | Stadtmiller et al. |
| 2005/0170308 | A1 | | 8/2005 | Lai et al. |

FOREIGN PATENT DOCUMENTS

WO    WO 98/20805    5/1998

* cited by examiner

*Primary Examiner*—John J Wilson
(74) *Attorney, Agent, or Firm*—James D. Christoff

(57) ABSTRACT

An orthodontic appliance includes a latch that comprises at least one clip with a region for receiving an archwire. The clip also includes a recess for receiving a post of the appliance and for coupling the clip to remaining components of the appliance. The clip includes at least one protrusion that extends between the post-receiving recess and the archwire-receiving region, and the protrusion serves to retain the clip in place on the post.

23 Claims, 7 Drawing Sheets

SELF-LIGATING ORTHODONTIC APPLIANCE WITH CLIP

CROSS REFERENCE TO RELATED APPLICATIONS

This application is a continuation-in-part of application Ser. No. 10/900,779, filed Jul. 28, 2004 now abandoned.

BACKGROUND OF THE INVENTION

1. Field of the Invention

This invention broadly relates to appliances that are used in the course of orthodontic treatment. More particularly, the present invention relates to a self-ligating orthodontic appliance such as a bracket or molar appliance having a latch that releasably retains an archwire in an archwire slot of the appliance.

2. Description of the Related Art

Orthodontic therapy is a specialized type of treatment within the field of dentistry, and involves movement of malpositioned teeth to orthodontically correct locations. Orthodontic treatment typically enhances the aesthetic appearance of the teeth, particularly in instances when the patient's front teeth are malpositioned or crooked. Orthodontic treatment can also improve the patient's occlusion so that the teeth function better with each other during mastication.

Many types of orthodontic treatment programs involve the use of a set of tiny appliances and wires that are commonly known collectively as "braces". During such treatment programs, small slotted appliances known as brackets are fixed to the patient's anterior, cuspid and bicuspid teeth, and an archwire is inserted into the slot of each bracket. The archwire forms a track to guide movement of the teeth to orthodontically correct locations. End sections of the archwires are typically captured in molar appliances that are fixed to the patient's molar teeth.

Recently, there has been increased interest in orthodontic appliances that have a latch for retaining the archwire in the archwire slot. Appliances of this type are widely known as self-ligating appliances and often obviate the need to use ligatures (such as wire ties or elastomeric O-rings) for retaining the archwire in the archwire slots. Improved self-ligating orthodontic appliances having a self-releasing latch are described in applicant's U.S. Pat. Nos. 6,302,688 and 6,582,226.

A recently introduced self-ligating appliance known as "SMARTCLIP" brand appliance from 3M Unitek Corporation has a latch that comprises two resilient clips, and each clip has a generally "C"-shaped configuration. The clips spread open to admit an archwire into an archwire slot of the appliance. Each clip is connected to a body of the appliance by a post that extends through the clip, and an outwardly extending base of the appliance helps to retain the clip in place on the post.

SUMMARY OF THE INVENTION

The present invention is directed toward a self-ligating orthodontic appliance having a latch that includes at least one clip. Each clip is connected to remaining components of the appliance by a post that extends through a recess of the clip. Each clip also has at least one protrusion that extends along a side of the post for retaining the clip in place.

In more detail, the present invention is directed in one aspect to an orthodontic appliance that comprises a base, a body extending outwardly from the base and an archwire slot extending across the appliance in a generally mesial-distal direction. The appliance also includes a post extending outwardly from the body, and a latch for releasably retaining an archwire in the archwire slot. The latch comprises a clip with a region next to the archwire slot for receiving the archwire. The clip also includes a recess that receives the post, and the recess is in communication with the archwire-receiving region. The post includes a side that faces the region. The clip also includes at least one protrusion that extends along the side of the post between the region and the recess.

Another aspect of the present invention is also directed toward an orthodontic appliance that comprises a base, a body extending outwardly from the base and an archwire slot extending across the appliance in a generally mesial-distal direction. The appliance further comprises a post extending outwardly from the body and a latch for releasably retaining an archwire in the archwire slot. The latch comprises a clip with a region next to the archwire slot for receiving an archwire. The clip also includes a recess that receives the post, and the recess is in communication with the archwire-receiving region. The post includes a side that faces the region. The clip also includes two protrusions that extend in opposite directions toward each other along the side of the post.

Advantageously, it has been found that the clip of the present invention enables the archwire to be inserted into the archwire-receiving region with less force than might be otherwise expected. Consequently, the practitioner is able to ligate the archwire to the appliance with less force and as a result the procedure is less painful to the patient. This feature is particularly important for patients with teeth that are somewhat mobile due to previous orthodontic therapy since those teeth are known to be more sensitive to pain caused by the pressure of external forces.

Additional aspects and features of the invention are set out in the detailed description that follows and are illustrated in the accompanying drawings.

DEFINITIONS

Figure 1:
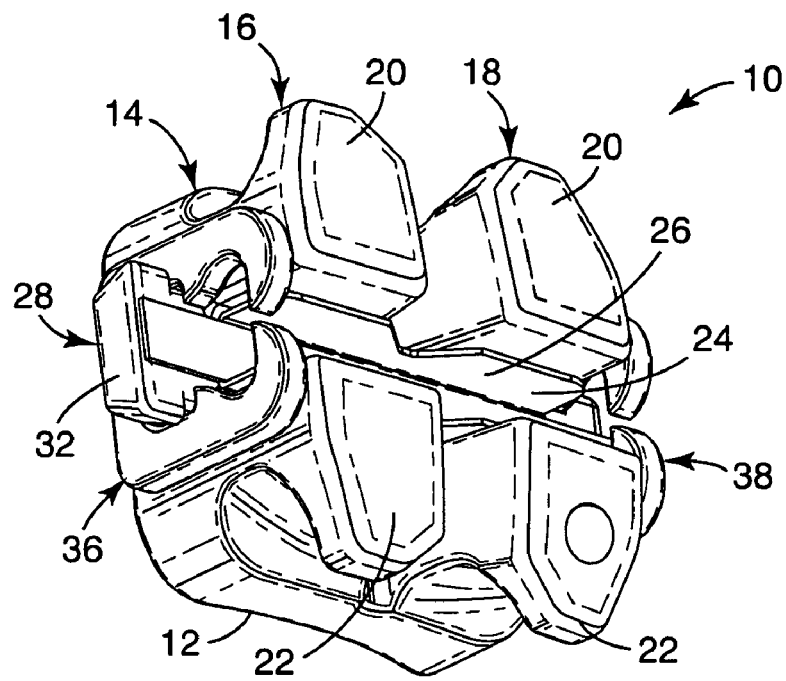
FIG. 1 is a perspective view of an orthodontic appliance constructed in accordance with one embodiment of the present invention, looking at the appliance toward its mesial, buccolabial and gingival sides.

"Mesial" means in a direction toward the center of the patient's curved dental arch.

"Distal" means in a direction away from the center of the patient's curved dental arch.

"Occlusal" means in a direction toward the outer tips of the patient's teeth.

"Gingival" means in a direction toward the patient's gums or gingiva.

"Buccolabial" means in a direction toward the patient's lips or cheeks.

"Lingual" means in a direction toward the patient's tongue.

DETAILED DESCRIPTION OF THE PREFERRED EMBODIMENTS

An orthodontic appliance constructed in accordance with one embodiment of the present invention is illustrated in FIGS. 1–8 and is broadly designated by the numeral 10. The appliance 10 in this instance is an orthodontic bracket that is adapted to be secured to an enamel surface of a patient's tooth, such as a buccolabial tooth surface. Alternatively, the appliance could be a molar appliance, an appliance for attachment to a lingual tooth surface, or any other appliance that is adapted to receive an archwire for controlling movement of the associated tooth during the course of orthodontic therapy.

The appliance 10 includes a base 12 for bonding the appliance 10 directly to the patient's tooth enamel by the use of an adhesive. Preferably, the base 12 has an outwardly facing concave compound contour that matches the convex compound contour of the patient's tooth surface to which it is bonded. Optionally, the base 12 is provided with grooves, particles, recesses, undercuts, a chemical bond enhancement material or any other material or structure, or any combination of the foregoing that facilitates bonding of the appliance 10 directly to the patient's tooth surface.

A body 14 extends outwardly from the base 12 in a generally buccolabial direction. The body 14 includes a mesial body portion 16 and a distal body portion 18 that is spaced from the mesial body portion 16. In this embodiment, each of the portions 16, 18 includes an occlusal tiewing 20 and a gingival tiewing 22, although one or more of the tiewings 20, 22 could be omitted if desired.

Figure 2:
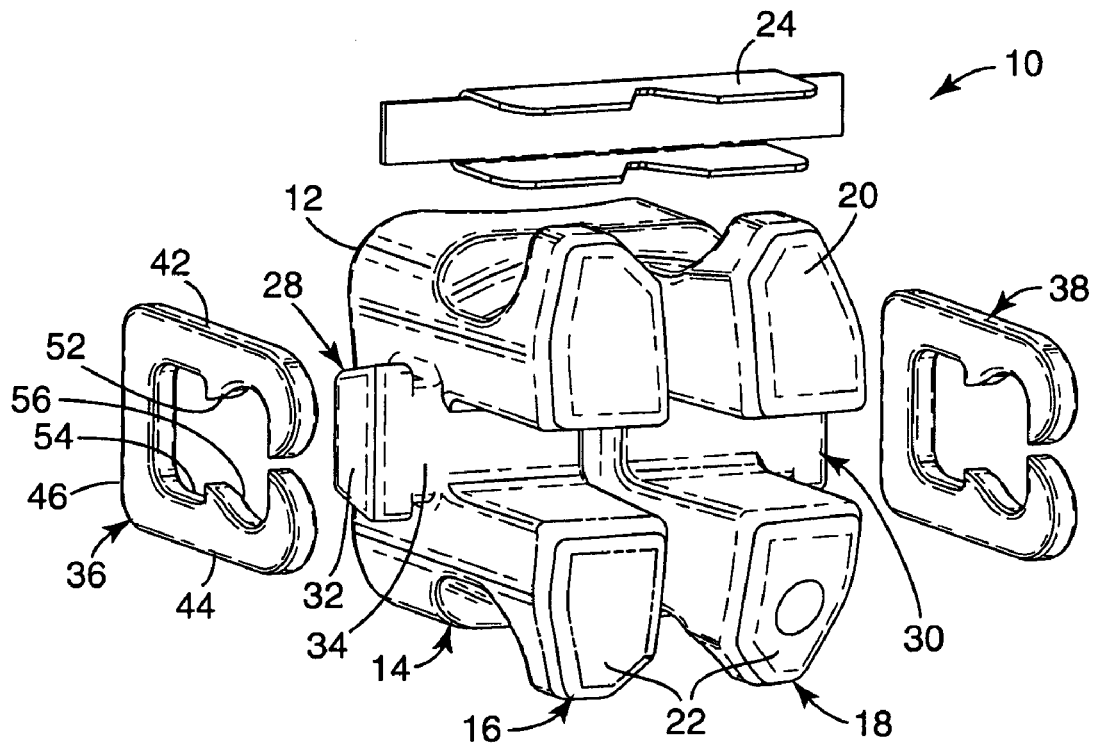
FIG. 2 is an exploded perspective view of the appliance depicted in FIG. 1, looking at the appliance toward its mesial, buccolabial and occlusal sides.
Figure 3:
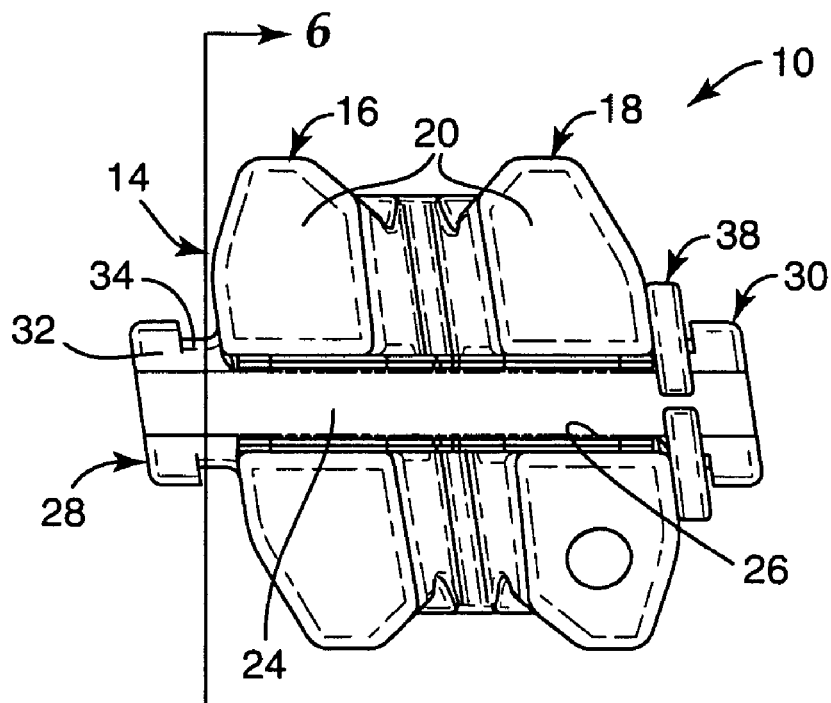
FIG. 3 is an assembled, front elevational view of the appliance shown in FIGS. 1 and 2, looking at the appliance toward its buccolabial side, and wherein one clip of the appliance has been omitted for purposes of illustration.
Figure 4:
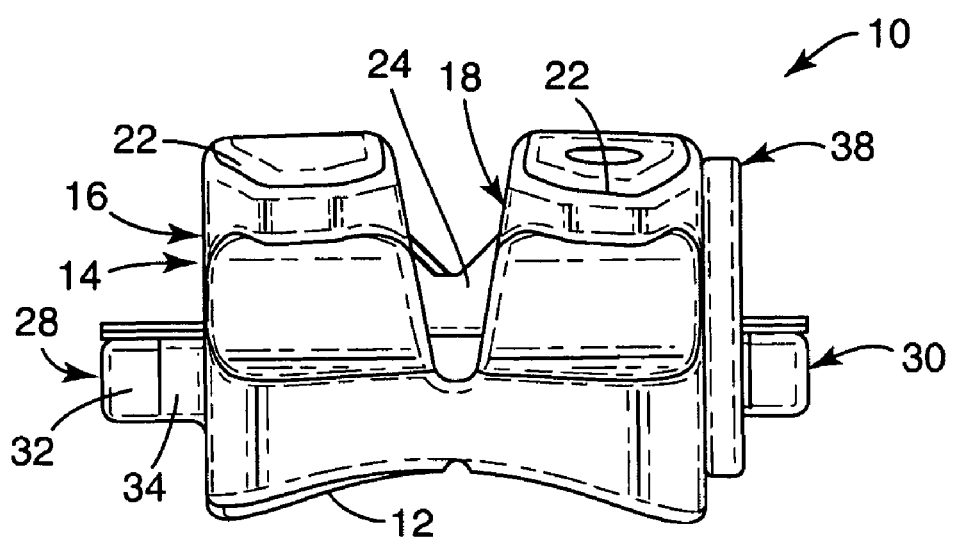
FIG. 4 is a bottom view of the appliance illustrated in FIG. 3, looking at the appliance toward its gingival side.

Preferably, and as shown in FIGS. 1–3, the body 14 (including the body portions 16, 18) is integrally connected to the base 12, and the body 14 and the base 12 form a single, unitary component. However, other constructions are also possible. For example, if the base and the body are made of a metallic material, the base could be manufactured separately from the body and later welded or brazed to the body during an assembly operation.

The appliance 10 also includes an archwire slot liner 24 that is fixed to the body portions 16, 18. The archwire slot liner 24 defines occlusal, gingival and lingual sides of an archwire slot 26. The archwire slot 26 longitudinally extends in a generally mesial-distal direction across the appliance 10, including through a channel of the body portions 16, 18. However, the archwire slot liner 24 is optional and may be omitted. If the archwire slot liner 24 is omitted, the channel of the body portions 16, 18 is made smaller in order to match the cross-sectional area of the archwire and serve as an archwire slot.

The base 12, the body 14 and the archwire slot liner 24 are preferably similar to the corresponding components of the appliances described in U.S. Pat. Nos. 5,439,379 and 5,366,372. Preferably, the base 12 and the body 14 are made of a transparent monocrystalline ceramic material or a translucent polycrystalline ceramic material such as alumina, and the archwire slot liner 24 is made of a metallic material. Examples of suitable materials and methods for constructing the archwire slot liner 24, as well as suitable methods of attaching the archwire slot liner 24 to the body portions 16, 18 are described in U.S. Pat. Nos. 5,358,402 and 5,380,196.

Each of the tiewings 20, 22 extends over a recess or notch for receiving a ligature (not shown). However, the provision of the tiewings 20, 22 and the use of a ligature are optional and may only be needed in certain instances, such as in instances where the tooth is severely malpositioned during the initial stages of treatment. Optionally, the tiewings 20, 22 and the ligature-receiving recesses are constructed as set out in applicant's co-pending U.S. Patent Application Publication No. 2005/0170308, Aug. 4, 2005 and entitled "ORTHODONTIC BRACKET WITH REINFORCED TIEWINGS".

The appliance 10 includes a mesial post 28 and a distal post 30 that are integrally connected to the mesial body portion 16 and the distal body portion 18 respectively. The posts 28, 30 extend outwardly in opposite directions away from each other and from the body 14. Preferably, each post 28, 30 extends along a reference axis that is parallel to the longitudinal axis of the archwire slot 26. As shown for example in FIGS. 4–6, the posts 28, 30 are located in a lingual direction relative to the archwire slot 26.

Figure 6:
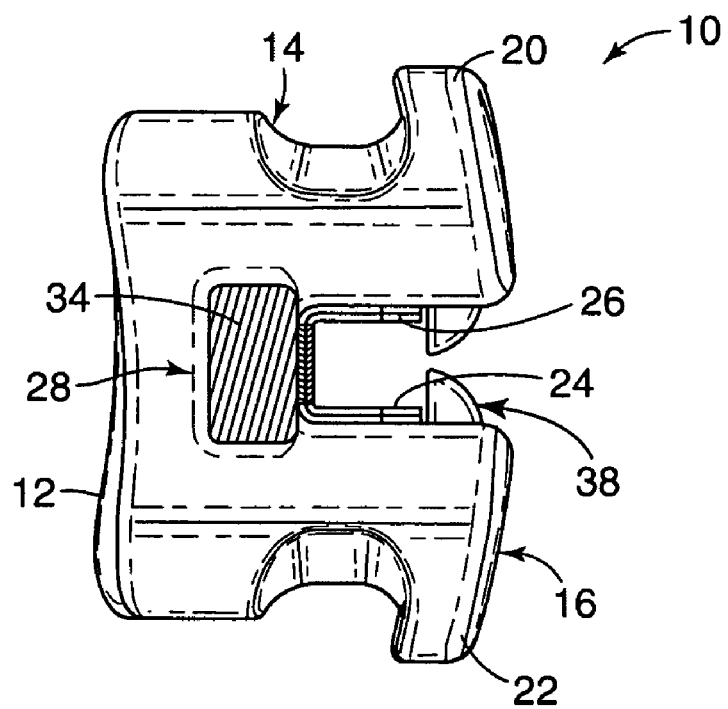
FIG. 6 is a side cross-sectional view taken along lines 6—6 of FIG. 3, showing among other things the configuration of a neck of a post of the appliance.

The mesial post 28 includes an outermost head 32 and a neck 34 that integrally interconnects the head 32 and the mesial body portion 16. As depicted in FIG. 6, the neck 34 has a generally rectangular cross-sectional configuration when considered in reference planes perpendicular to the reference axis along which the post 28 extends or when considered in reference planes generally perpendicular to a mesial-distal axis. Preferably, the occlusal, gingival and lingual sides of the neck 34 in regions along the innermost or distal end of the neck 34 include curved or chamfered sections that are connected to the mesial side of the mesial body portion 16, for enhancing the strength of the connection between the mesial post 28 and the body 14.

Figure 5:
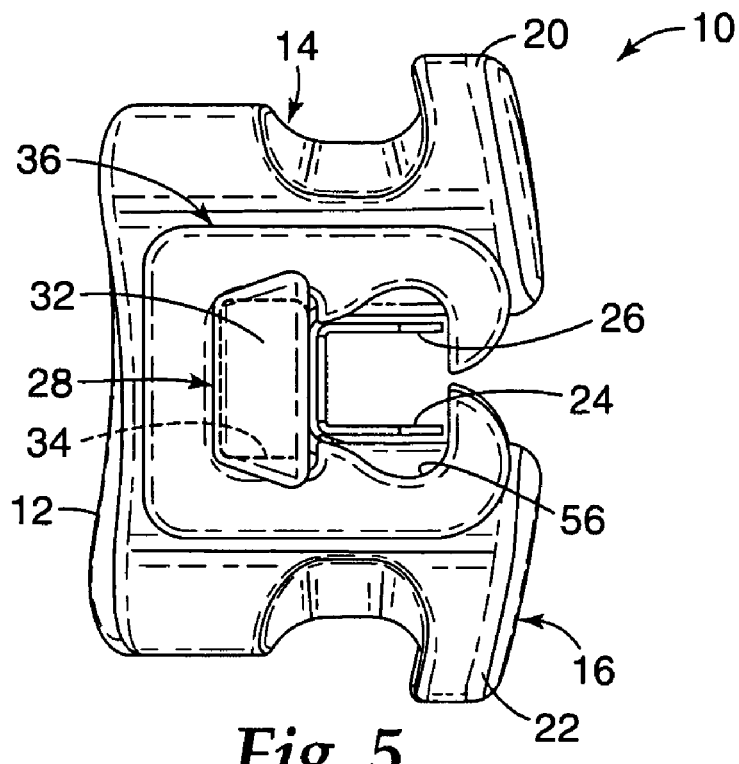
FIG. 5 is a side elevational view of the appliance shown in FIGS. 1–4, looking at the appliance toward its mesial side and illustrating the clip in place.

As shown for example in FIG. 5, the head 32 of the post 28 has a generally trapezoidal configuration when viewed in a distal direction, or when viewed in reference planes that are perpendicular to the reference axis along which the post 28 extends. FIG. 5 also illustrates in dashed lines the cross-sectional shape of the neck 34 for purposes of comparison. As illustrated, the height of the neck 34 and the height of the head 32 are essentially the same along the lingual side of the post 28 when considered in directions along an occlusal-gingival reference axis (i.e. along a vertical axis when viewing FIGS. 5–8). However, along the buccolabial side of the post 28, the height of the head 32 is greater than the height of the neck 34 when considered in directions along an occlusal-gingival reference axis.

The head 32 extends outwardly past the neck 34 a certain distance when considered in reference planes perpendicular to a mesial-distal reference axis or when considered in reference planes perpendicular to the reference axis along which the post 28 extends. In the illustrated embodiment, the head 32 extends outwardly past the neck 34 in at least one, and preferably in both directions along an occlusal-gingival reference axis, or in directions along a vertical axis when viewing FIGS. 5–8. In the illustrated embodiment, this certain distance is determined by adding the distance that the head 32 extends past the neck 34 in an occlusal direction to the distance that the head 32 extends past the neck 34 in a gingival direction. This certain distance decreases as the lingual side of the post 28 is approached and as a third section 46 of the clip 36 (as described below) is approached. This relationship is shown by the dashed lines in FIG. 5 illustrating the occlusal and gingival sides of the neck 34, in comparison to the full lines that depict the occlusal and gingival sides of the head 32. Preferably, this certain distance is zero or approximately zero in regions adjacent the third section 46.

In this embodiment, the archwire slot liner 24 has a rectangular mesial extension that extends over the buccolabial side of the post 28 and is connected to the same by the methods described in U.S. Pat. Nos. 5,358,402 and 5,380,196. However, other constructions are also possible. For example, the archwire slot liner 24 may have a mesial extension that is somewhat "T"-shaped, to match the generally "T"-shaped configuration presented by the neck 34 and the head 32 as depicted in FIG. 3. As yet another option, the mesial extension of the archwire slot liner 24 may be omitted such that the mesial end of the archwire slot liner 28 is flush with the mesial side of the mesial body portion 16.

The appliance 10 also includes a latch for releasably retaining an archwire in the archwire slot 26. In the illustrated embodiment, the latch includes a mesial clip 36 that is connected to the mesial post 28, and a distal clip 38 that is connected to the distal post 30. The mesial clip 36 is omitted from FIGS. 3, 4 and 6 for purposes of illustration.

Figure 7:
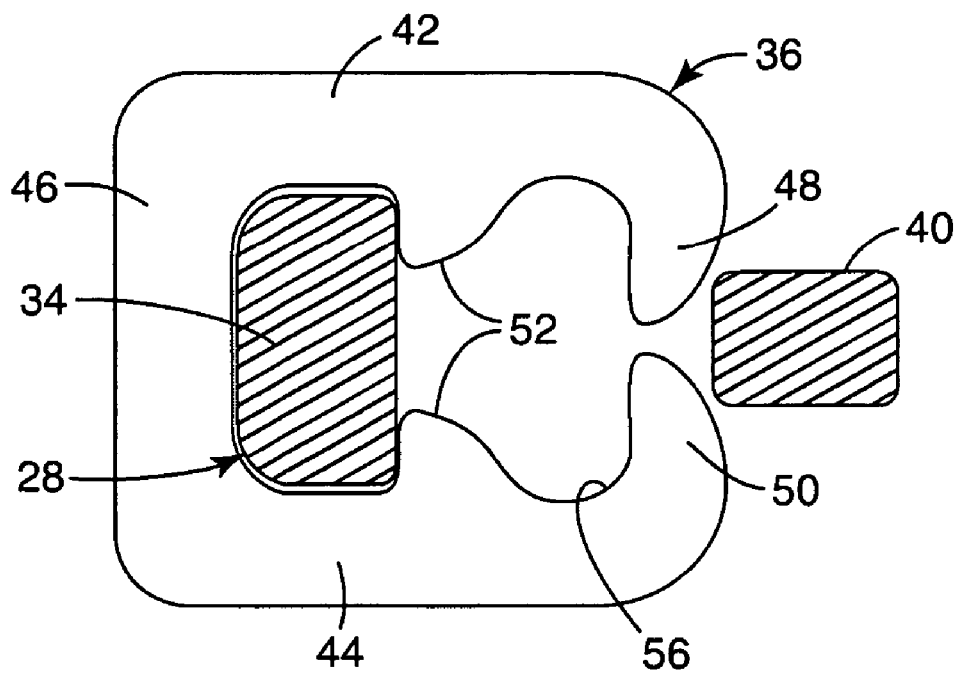
FIG. 7 is a view of the neck and clip alone, along with an exemplary archwire that is about to be received in an archwire slot of the appliance.
Figure 8:
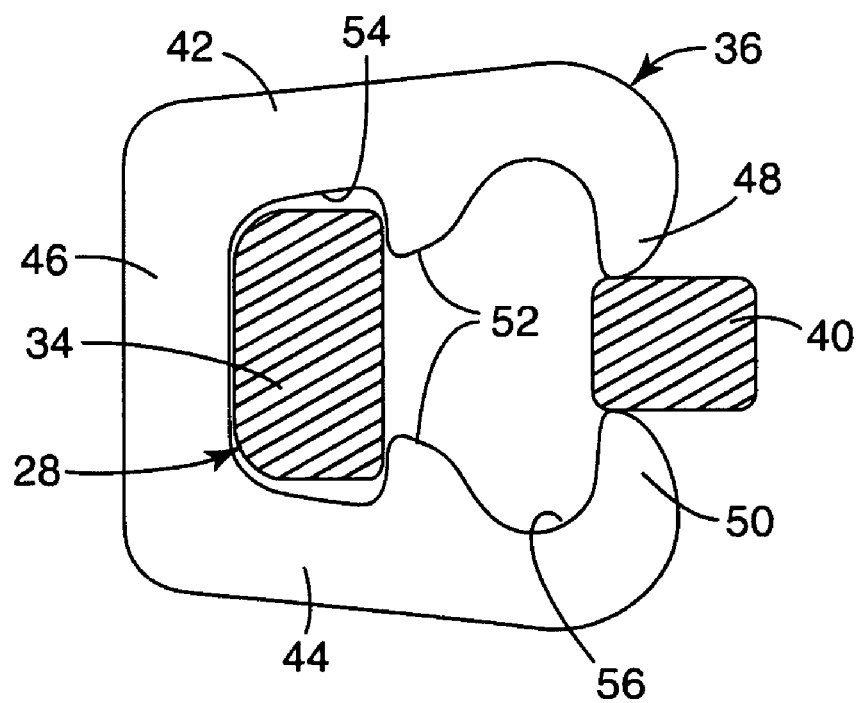
FIG. 8 is a view somewhat similar to FIG. 7 except that the clip is shown in an open position as it might appear during insertion of the archwire into the archwire slot.
Figure 9:
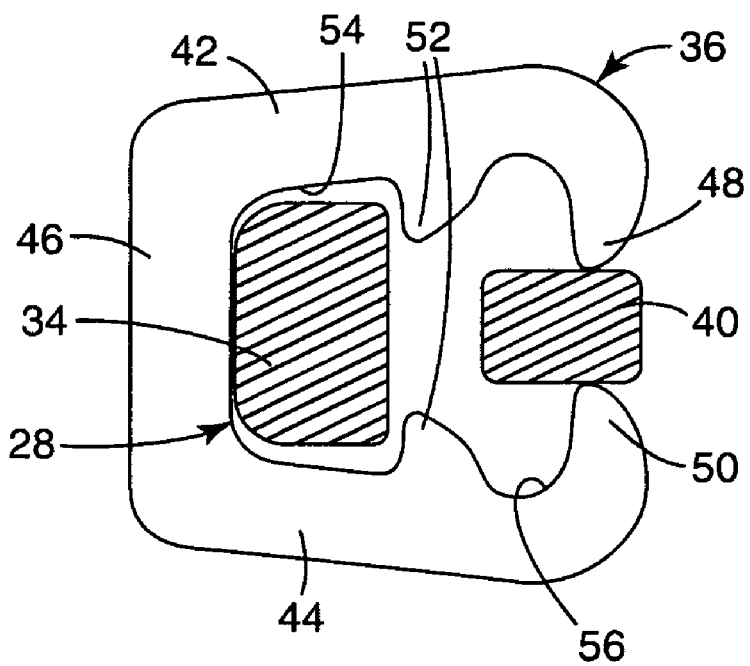
FIG. 9 is a view somewhat similar to FIG. 8 except that the clip is shown in an open position as it might appear during release of the archwire from the archwire slot.

The mesial clip 36, the neck 34 and an exemplary archwire 40 are shown alone in FIGS. 7 and 8. The mesial clip 36 includes an elongated occlusal or first section 42, an elongated second or gingival section 44 and an elongated lingual or third section 46. The first and second sections 42, 44 extend in generally parallel directions that lie along a generally buccolabial-lingual reference axis when the clip 36 is relaxed, and the third section 46 extends in a generally occlusal-gingival direction perpendicular to the direction of extension of the sections 42, 44.

The third section 46 also integrally connects the first and second sections 42, 44. Additionally, outer ends of the sections 42, 44 are integrally connected to arm portions 48, 50 respectively. A buccolabial edge of each arm portion 42, 44 is smoothly curved in an arc about a mesial-distal reference axis.

The sections 42, 44, 46 extend along the occlusal, gingival and lingual sides of the neck 34 respectively. In addition, each of the sections 42, 44 includes a somewhat triangular-shaped protrusion 52 that extends along a portion of the buccolabial side of the neck 34. A rear (lingual) portion of the first and second sections 42, 44, along with the third section 46 and the protrusions 52 together at least partially define a recess 54 (see FIGS. 2 and 8) for receiving the neck 34 of the post 28. Outer ends of the sections 42, 44 include arm portions 48, 50 respectively, each of which has a smoothly curved outer edge.

A front (buccolabial) portion of the first and second sections 42, 44, along with arm portions 48, 50 and a portion of the buccolabial side of the neck 34, together at least partially define a region 56 for receiving the archwire 40. As shown for example in FIG. 5, the region 56 is aligned with the archwire slot 26. Overall, the clip 36 presents a generally "C"-shaped configuration when looking in a mesial or distal direction.

The clip 36 is shown in its normal, relaxed orientation in FIGS. 1, 2, 5 and 7. However, the arm portions 48, 50 are movable away from each other in order to admit the archwire 40 into the archwire-receiving region 56 when desired. To this end, the first and second sections 42, 44 deflect outwardly when the clip 36 is opened and bend in respective arcs away from each other in order to enable the arm portions 48, 50 to move apart from each other.

The smooth, outer edge of the arm portions 48, 50 enables the clip 36 to open and admit the archwire 40 into the region 56 by pressing the archwire 40 against the outer curved edges of the arm portions 48, 50. As pressure is exerted by the archwire 40 on the curved edges, the first and second sections 42, 44 deflect away from each other in order to admit the archwire 40 into the region 56. FIG. 8 is an exemplary illustration showing the clip 36 opened, wherein the arm portions 48, 50 have been moved apart from each other a sufficient distance to permit passage of the archwire 40 into the region 56.

As the clip 36 is opened, the protrusions 52 slide across the buccolabial side of the neck 34. However, the protrusions 52 extend inwardly and toward each other a distance sufficient to remain in contact with the buccolabial side of the neck 34 as the clip 36 is opened. As such, the clip 36 remains coupled to the post 28 during such opening movements.

Once the archwire 40 is received in the region 56, the inherent resiliency of the clip 36, and particularly the resiliency of the first and second sections 42, 44, enables the arm portions 48, 50 to spring back toward each other and toward their normal, relaxed configuration as shown in FIGS. 1, 2, 5 and 7 in order to retain the archwire 40 in the archwire slot 26. Preferably, but not necessarily, the region 56 is somewhat larger than the cross-section of the archwire 40 in directions along both an occlusal-gingival reference axis as well as along a buccolabial-lingual reference axis, in order to avoid firm contact between the clip 36 and the archwire 40. The spaces between the clip 36 and the archwire 40 provide what is often referred to as "passive" ligation.

The clip 36 (including the first and second sections 42, 44) is sufficiently stiff to retain the archwire 40 in the archwire slot 26 during the course of treatment so long as the forces exerted by the archwire 40 on the appliance 10 are below a certain minimum value in a generally buccolabial direction (more particularly, in a direction opposite to the direction of insertion of the archwire 40 into the archwire slot 26). However, whenever the forces exerted by the archwire 40 on the appliance 10 in the same direction are greater than the minimum value, as might occur when unexpectedly high forces are encountered, the first and second sections 42, 44 deflect outwardly and the arm portions 48, 50 move apart from each other to open the clip 36 and release the archwire 40 from the archwire slot 26. Further details regarding such forces are described in the aforementioned U.S. Pat. Nos. 6,302,688 and 6,582,226.

Preferably, the clip 36 is substantially identical to the clip 38 and the post 28 is substantially identical in mirror image to the post 30. The latch, comprising the clips 36, 38, preferably releases the archwire 40 from the archwire slot 26 in a generally buccolabial direction whenever the archwire 40 exerts a force in the same direction on the appliance 10 that is in the range of about 0.2 lb (0.1 kg) to about 11 lb (5 kg), more preferably in the range of about 0.4 lb (0.2 kg) to about 5.5 lb (2.5 kg), and most preferably in the range of about 0.75 lb (0.34 kg) to about 3.0 lb (1.4 kg). Preferably, the minimum value is sufficiently high to prevent the archwire from unintentionally releasing from the archwire slot 26 during the normal course of orthodontic treatment. As such, the archwire 40 can exert forces on the appliance 10 sufficient to carry out the treatment program and move the associated teeth as desired.

Preferably, the minimum value for self-release (i.e., self-opening) of the latch is substantially less than the force required in the same direction to debond the appliance 10 from the associated tooth. The minimum value for self-release of the latch is preferably less than about one-half of the force required in the same direction to debond the appliance 10 from the associated tooth. For example, if the expected bond strength of the adhesive bond between the appliance 10 and the associated tooth is 16 lbs (7.2 kg) in a buccolabial direction, the latch is constructed to self-release the archwire 40 whenever the archwire 40 exerts a force in the same buccolabial direction on the appliance 10 that is somewhat greater than about 8 lbs (3.6 kg).

To determine the force to release the latch, a section of archwire is selected having an area in longitudinally transverse sections that is complemental to (i.e., substantially fills) the cross-sectional area of the archwire slot 26. Next, a sling is constructed and is connected to the archwire section at locations closely adjacent, but not in contact with the heads of the posts 28, 30 including the head 32. Optionally, the sling is welded or brazed to the archwire section. Next, the sling is pulled away from the appliance 10 while the appliance 10 is held in a stationary position, taking care to ensure that the longitudinal axis of the archwire section does not tip relative to the longitudinal axis of the archwire slot 26. The force to release the latch may be determined by use of an Instron testing apparatus connected to the sling, using a crosshead speed of 0.5 in/min (1.3 cm/min). Alternatively, a shaker apparatus (such as Model 300 from APS Dynamics of Carlsbad, Calif.) may be used along with a force transducer (such as model 208C01 from PCB of Buffalo, N.Y.) to measure the force.

Preferably, the distance between the opposed ends of the arm portions 48, 50 is less than the overall occlusal-gingival dimension of the smallest archwire 40 expected to be used during the course of treatment. The archwire 40 need not fill the archwire slot 26 and flatly engage the wall portions defining the archwire slot 26 in all instances. For example, a somewhat smaller wire, and perhaps an archwire 40 having a circular cross-sectional shape, may be used during a portion of the treatment program. The distance between the opposed ends of the arm portions 48, 50 is preferably selected so that a variety of archwires of different cross-sectional configurations may be used in connection with the appliance 10.

Preferably, and as mentioned above, the distal clip 38 is substantially identical to the mesial clip 36. Optionally, however, it is possible to construct the clips 36, 38 somewhat differently to address certain circumstances. For example, if a malpositioned tooth is initially oriented such that its mesial side is rotated in a lingual direction, it may be desirable to increase the stiffness of the mesial clip 36 so that a somewhat greater force is needed to release the archwire 40 from the archwire slot 26 in comparison to the force needed to release the archwire 40 from the distal clip 38. Other options are also possible.

Optionally, the spring clips 36, 38 are cut from a flat section of metallic stock material. Suitable metallic materials include shape memory alloys such as alloys of nitinol and beta-titanium. The clips 36, 38 may be cut from the stock material using a stamping, die cutting, chemical etching, EDM (electrical discharge machining), laser cutting or water jet cutting process. As another option, the clips 36, 38 could be formed and then heat-treated to set their shapes.

As presently preferred, the clips 36, 38 are made from flat annealed superelastic material (such as nitinol) having a pickled surface. Preferred nitinol materials have a nickel content of 55.97% by weight and an $A_f$ of 10°±5° C. The nitinol is cold worked to 37.5% and has a thickness in the range of about 0.012 in. (0.3 mm) to about 0.016 in. (0.4 mm). The clips 36, 38 are first cut in a rough cutting EDM process, then cut along their edges for an additional one or more times using an EDM process in order to smooth the edges. Alternatively, a laser cutting process or chemical etching process could be used to make the clips 36, 38. Preferably, the clips 36, 38 are constructed so that the longitudinal direction of the clip material, or the principal direction of grain flow of the clip material, is substantially parallel to the direction of extension of the first and second sections 42, 44 (i.e. a generally buccolabial direction in the illustrated embodiment).

Subsequent to the EDM, laser cutting or chemical etching process, the clips 36, 38 are tumbled in order to further round their edges. An example of a suitable tumbling machine is model LC-600-2+2 from Richwood Industries. Using a small barrel, and a machine speed of 200 rpm, the clips are tumbled for about 2 hours in 500 cc of water and tumbling media. An example of suitable tumbling media is a mixture of 500 cc of ceramic media (shaped ACC, type M, size ³⁄₁₆×³⁄₈ (4.7 mm×9.5 mm)), 25 cc of white alumina powder no. 40, and 25 cc of soap powder compound no. 43, all from Richwood Industries. The tumbled clips are then polished for one-half hour in an ultrasonic screen barrel in a tank of solution. An example of a suitable solution is 3 liters of deionized water, 3 liters of pickling solution and 0.6 liter of hydrogen peroxide. A suitable pickling solution is No. TI121 Pickling Solution from Aya International of Los Angeles, Calif.

Other optional aspects of the clips 36, 38 are described in applicant's published U.S. patent application entitled "ORTHODONTIC APPLIANCE WITH FATIGUE-RESISTANT ARCHWIRE RETAINING LATCH"; No. 2004/0086825, published May 18, 2004.

During manufacture of the appliance 10, the archwire slot liner 24 is affixed to the body 14 and the clips 36, 38 are then assembled to the posts 28, 30 respectively. To connect the clip 36 to the post 28, the clip 36 is opened by moving the sections 42, 44 in directions away from each other a distance sufficient to clear the head 32 and enable the neck 34 to be received in the recess 54 by moving the clip 36 in a distal direction. Next, pressure on the sections 42, 44 is relieved and the clip 36 springs back to its normal, relaxed configuration such as shown in FIGS. 1, 2, 5 and 7, whereupon it is held in place by the head 32.

The present invention provides a significant advantage, in that the protrusions 52 serve to hold the clip 36 in place on the post 28. In particular, the protrusions 52 help prevent the clip 36 from moving in a lingual direction and disengaging the post 28 as might occur, for example, when the archwire 40 is pressed against the arm portions 48, 50 for insertion into the archwire slot 26. Such construction avoids the need for a base flange or other structure located on the lingual side of the third section 46, which in turn enables the base or "footprint" of the appliance 10 to be somewhat smaller than might otherwise be expected.

Figure 10:
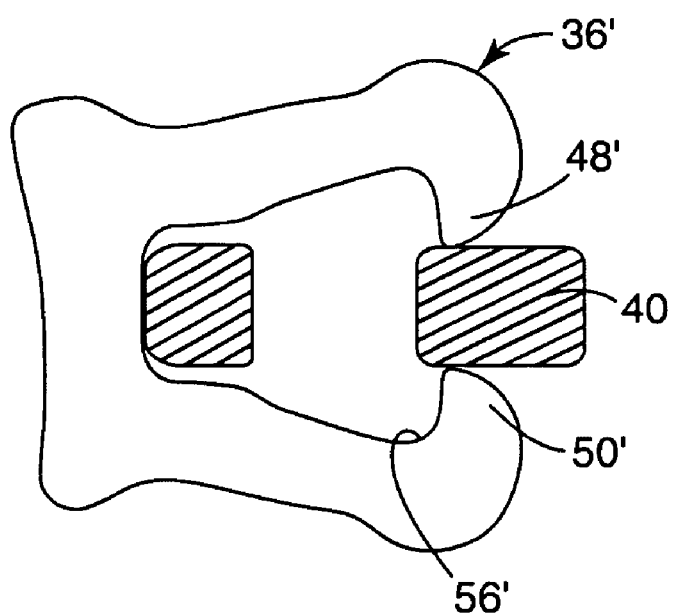
FIG. 10 is a view somewhat similar to FIG. 8 except that a clip of prior art construction is illustrated for purposes of comparison.

Furthermore, the present invention surprisingly allows the archwire 40 to be inserted into the archwire slot 26 with less force than expected, while the force needed to self-release the latch remains approximately the same. In one experimental analysis done by computer, using software "ANSYS 8.0" from ANSYS, Inc. of Canonsburg, Pa., the force needed to ligate the archwire to the appliance and the force needed to release the archwire from the appliance were determined for an appliance having a clip constructed as shown in FIG. 8 and for a prior art appliance having a clip constructed as shown in FIG. 10. A graph depicting the results determined for archwire ligation is set out in FIG. 11, and a graph depicting the results determined for archwire release is set out in FIG. 12.

Figure 11:
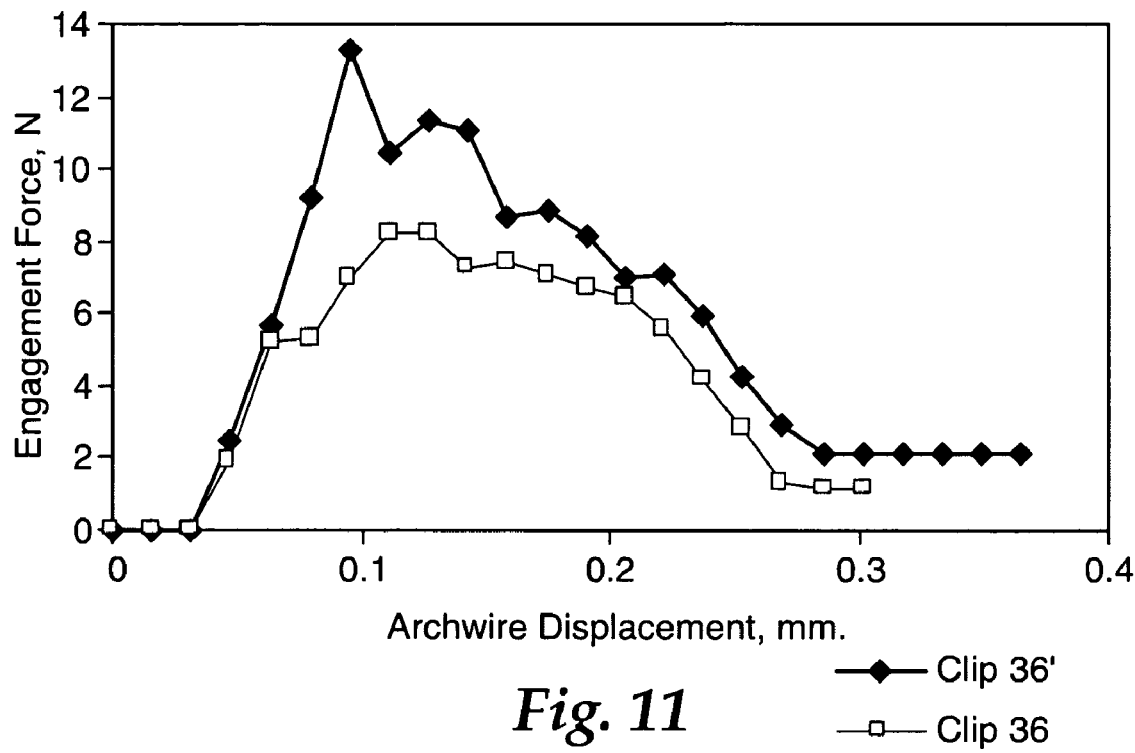
FIG. 11 is a graph depicting the force needed to insert an archwire into an archwire slot of an appliance having the clip shown in FIG. 8, along with the force needed to insert an archwire into an archwire slot of an appliance having the clip shown in FIG. 10.

The graph of FIG. 11 shows that a significantly higher force is needed for archwire ligation using the clip 36' depicted in FIG. 10 in comparison to the force needed for archwire ligation using the clip 36 depicted in FIG. 8. In FIG. 11, the maximum force needed to push the archwire 40 in a lingual direction to ligate the archwire to the appliance 10' shown in FIG. 10 (i.e., the maximum force needed to push the archwire 40 in a lingual direction in order to spread apart arm portions 48', 50' and move the archwire 40 into region 56') was 13.3 Newtons. By contrast, the maximum force needed to push the archwire 40 in a lingual direction to ligate the archwire 40 to the appliance 10 having the clip 36 was 8.3 Newtons.

Figure 12:
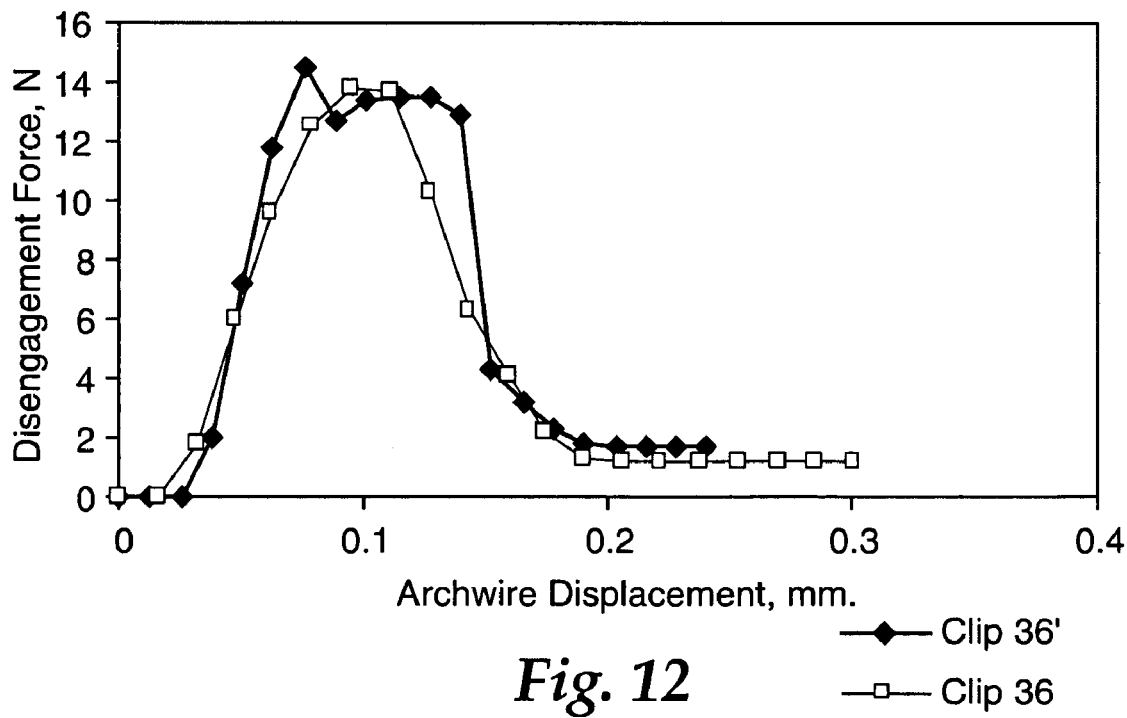
FIG. 12 is a graph somewhat similar to FIG. 11 except that the forces needed to release an archwire from the archwire slot of the appliances are shown.

The graph set out in FIG. 12 shows that the force needed to disengage or release the archwire from the archwire slot of both appliances is approximately the same. This is an advantage in that the likelihood of unintentional release of the archwire from both appliances during the course of treatment is also approximately the same. In FIG. 12, a maximum force of 14.5 Newtons exerted on the archwire 40 in a buccolabial direction was needed to spread apart the arm portions 48', 50' and move the archwire 40 out of the region 56' in order to release the archwire 40 from the appliance. By contrast, the maximum force exerted on the archwire 40 in a buccolabial direction that was needed to release the archwire 40 from the appliance 10 was 13.8 Newtons.

In this experiment, both clips were made of the same material (super-elastic nitinol) and the thickness of the clips was 0.0128 inch (0.33 mm). In this experiment, the overall occlusal-gingival height and buccolabial-lingual width of the clip of the present invention were approximately 0.076 inch (1.88 mm) and 0.084 inch (2.13 mm) respectively. The occlusal-gingival height and buccolabial-lingual width for the clip 36' shown in FIG. 10 were approximately 0.064 inch (1.62 mm) and 0.079 inch (2.00 mm) respectively.

As a result, the present invention facilitates insertion of the archwire 40 into the archwire slot 26 without adversely affecting the self-releasing aspects of the latch to any significant extent. This feature is a particular advantage in that the practitioner may ligate the archwire 40 to the appliance 10 with less force than might be otherwise possible. This feature is also beneficial to the patient, since less force is exerted on the patient's teeth during ligation and as a consequence any pain experienced by the patient is correspondingly reduced.

It was also found in the computer analysis described above that the strain exerted on the clip 36 during archwire ligation and release is reduced in comparison to the clip 36' illustrated in FIG. 10. The reduction is strain results in a higher fatigue life and reduces the possibility of fracture of the clip 36 during opening of the clip 36.

Figure 13:
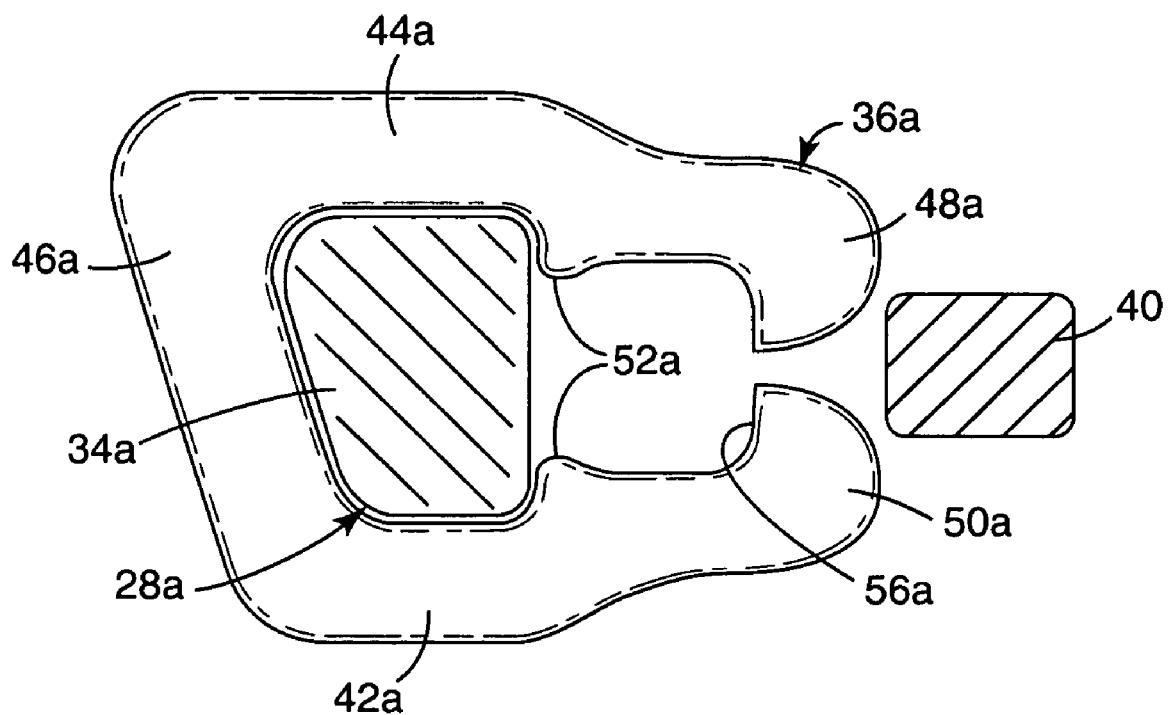
FIG. 13 is a view somewhat similar to FIG. 7 but showing a clip for an orthodontic appliance according to another embodiment of the invention.

FIG. 13 is an illustration somewhat similar to FIG. 7, but showing a clip for an orthodontic appliance in accordance with another embodiment of the invention. This appliance is somewhat similar to the appliance 10 shown in FIGS. 1–6, but is constructed with "torque in the base", wherein the bottom or lingual side of the archwire slot extends at a non-zero angle relative to the tooth-facing side of the base of the appliance. This appliance has two clips, one of which is shown and designated by the numeral 36a in FIG. 13.

The clip 36a is shown in its relaxed orientation in FIG. 13. The clip 36a includes an elongated occlusal or first section 42a, an elongated second or gingival section 44a and an elongated lingual or third section 46a. The first and second sections 42a, 44a extend in generally parallel directions that lie along a generally buccolabial-lingual reference axis when the clip 36a is relaxed.

The third section 46a extends at an angle other than 90 degrees relative to the direction of extension of the sections 42a, 44a, and at a non-zero angle relative to the lingual side of the archwire slot. Preferably, the third section 46a extends in a direction that is equal to the "torque" of the appliance. The torque of the appliance is equivalent to the angle between a reference plane containing the lingual side of the archwire slot and a certain reference axis. To determine the orientation of the reference axis, a reference line is extended in a lingual direction from the mesial-distal center and the occlusal-gingival center of the archwire slot. The reference axis extends in a plane that is perpendicular to a mesial-distal reference axis and is also tangent to the curved surface of the appliance base at the location where the reference line contacts the curved surface.

Preferably, the lingual edge of the third section 46a is closely adjacent the base such that there is little space between the lingual edge of the third section 46a and the surface of the tooth once the appliance is bonded to the tooth enamel. In this manner, the likelihood of a build-up of plaque next to the clip 36a is reduced. Optionally, this lingual edge is curved in a convex or in a concave direction.

The sections 42a, 44a, 46a extend along the occlusal, gingival and lingual sides respectively of a neck 34a of the appliance. The neck 34a is somewhat similar to the neck 34 described above, except that the neck 34a has a lingual side that extends at a non-zero angle relative to its buccolabial side, such that the lingual side of the neck extends in a direction parallel to the third section 46a. The neck 34a is part of a post 28a of the appliance, and the post 28a includes a head that is somewhat similar to the head 32.

Each of the sections 42a, 44a includes a somewhat triangular-shaped protrusion 52a that extends along a portion of the buccolabial side of the neck 34a. The third section 46a, the protrusions 52a, and a rear (lingual) portion of the first and section sections 42a, 44a together at least partially define a recess for receiving the neck 34a. A front (buccolabial) portion of the first and second sections 42a, 44a along with arm portions 48a, 50a and a portion of the buccolabial side of the neck 34a, together at least partially define a region 56a for receiving the archwire 40.

Figure 14:
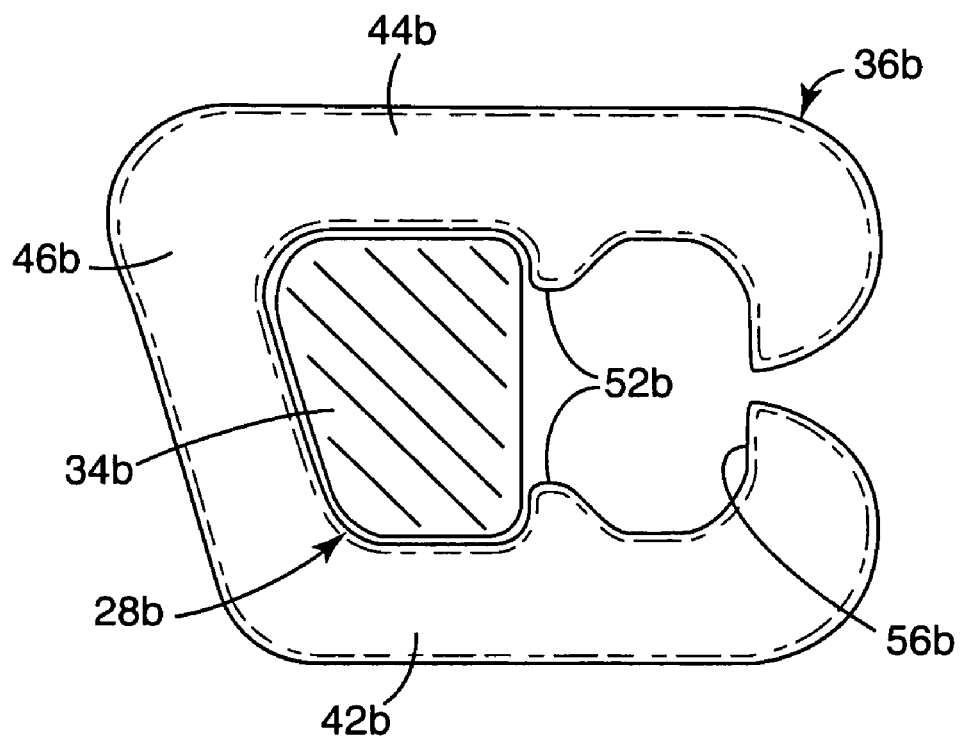
FIG. 14 is a view somewhat similar to FIG. 13 but showing a clip for an orthodontic appliance according to still another embodiment of the invention.

FIG. 14 is an illustration of a clip 36b for an orthodontic appliance in accordance with another embodiment of the invention. This appliance also has a latch with two clips, one of which is the clip 36b in FIG. 14.

The clip 36b has a first section 42b, a second section 44b and a third section 46b. The clip 36b also has an archwire-receiving region 56b between the first and second sections 42b, 44b. The third section 46b, like the third section 46a, extends at an angle other than 90 degrees relative to the direction of extension of the sections 42b, 44b. Preferably, the third section 46b extends in a direction that is equal to the torque of the base.

The clip 36b is somewhat similar to the clip 36a, except that the first and second sections 42b, 44b have straight outer edges. In addition, the archwire-receiving region 56b is somewhat larger than the archwire-receiving region 56a, which facilitates insertion of a tool for spreading the sections 42b, 44b apart during assembly of the clip 36b to the neck 34b of post 28b.

Except as described above, the clips 36a, 36b are somewhat similar to the clip 36 in construction as well as in function and operation.

A number of other constructions are also possible. For example, the body and/or base may be made of a metallic (such as stainless steel) or plastic material (such as fiber-reinforced polycarbonate) instead of the ceramic materials mentioned above. Furthermore, the archwire slot liner 24 is optional and may be omitted if desired.

All of the patents and patent applications mentioned above are hereby expressly incorporated by reference herein. The embodiments described in detail above and shown in the drawings are intended to exemplify the invention, and should not be deemed to limit the scope of the claims that follow.

The invention claimed is:

1. An orthodontic appliance comprising:
a base;
a body extending outwardly from the base;
an archwire slot extending across the appliance in a generally mesial-distal direction;
a post extending outwardly from the body; and
a latch for releasably retaining an archwire in the archwire slot, wherein the latch comprises a clip with a region next to the archwire slot for receiving an archwire, wherein the clip is connected to the post and has arm portions that are movable away from each other to an opened position to admit an archwire into the archwire-receiving region while the clip remains connected to the post and movable toward each other to retain an archwire in the archwire slot, wherein the clip also includes a recess that receives the post, wherein the recess is in communication with the archwire-receiving region, wherein the post includes a side that faces the region, and wherein the clip also includes at least one protrusion extending between the region and the recess and along the side of the post that faces the region when the arm portions are in the opened position.

2. An orthodontic appliance according to claim 1 wherein the protrusion is in contact with the post as an archwire is inserted into the archwire slot.

3. An orthodontic appliance according to claim 1 wherein the clip includes two protrusions that extended between the region and the recess, and wherein the protrusions extend inwardly in opposite directions toward each other.

4. An orthodontic appliance according to claim 1 wherein the clip includes a first section, a second section and a third section interconnecting the first section and the second section, and wherein the first section and the second section are movable away from each other to admit the post into the recess and are also movable away from each other to receive the archwire in the region.

5. An orthodontic appliance according to claim 4 wherein the protrusion is in contact with the post as an archwire is received in the region.

6. An orthodontic appliance according to claim 4 wherein the clip includes two protrusions that extend between the region and the recess, wherein the protrusions extend in opposite directions toward each other, wherein the side of the post has a certain size when considered in directions parallel to the directions of extension of the protrusions, and wherein the distance between the protrusions is smaller than the certain size.

7. An orthodontic appliance according to claim 6 wherein the certain size is determined in directions along an occlusal-gingival reference axis.

8. An orthodontic appliance according to claim 4 wherein the third section extends at an angle other than 90 degrees relative to the direction of extension of the first section and the second section.

9. An orthodontic appliance according to claim 1 wherein the post includes a head and a neck interconnecting the head and the body, and wherein the side of the post is located on the neck.

10. An orthodontic appliance according to claim 9 wherein the side of the post faces a buccolabial direction.

11. An orthodontic appliance according to claim 1 wherein the latch comprises two clips.

12. An orthodontic appliance according to claim 1 wherein the clip has an overall, generally "C"-shaped configuration.

13. An orthodontic appliance comprising:
a base;
a body extending outwardly from the base;
an archwire slot extending across the appliance in a generally mesial-distal direction;
a post extending outwardly from the body; and
a latch for releasably retaining an archwire in the archwire slot, wherein the latch comprises a clip with a region next to the archwire slot for receiving an archwire, wherein the clip is connected to the post and has arm portions that are movable away from each other to an opened position to admit an archwire into the archwire-receiving region wile the clip remains connected to the post and movable toward each other to retain an archwire in the archwire slot, wherein the clip also includes a recess that receives the post, wherein the recess is in communication with the archwire-receiving region, wherein the post includes a side that faces the region, and wherein the clip also includes two protrusions that extend in opposite directions toward each other along the side of the post that faces the region when the arm portions are in the opened position.

14. An orthodontic appliance according to claim 13 wherein the side of the post is a buccolabial side.

15. An orthodontic appliance according to claim 13 wherein the protrusions are in contact with the post as an archwire is inserted into the archwire slot.

16. An orthodontic appliance according to claim 13 wherein the clip includes a first section, a second section and a third section interconnecting the first section and the second section, and wherein the first section and the second section are movable away from each other to admit the post into the recess and are also movable away from each other to receive the archwire in the region.

17. An orthodontic appliance according to claim 16 wherein the protrusions are in contact with the post as an archwire is received in the region.

18. An orthodontic appliance according to claim 16 wherein one of the protrusions is part of the first section and wherein the other of the protrusions is part of the second section.

19. An orthodontic appliance according to claim 13 wherein the post includes a head and a neck interconnecting the head and the body, and wherein the side of the post is located on the neck.

20. An orthodontic appliance according to claim 19 wherein the side of the post faces a buccolabial direction.

21. An orthodontic appliance according to claim 13 wherein the latch comprises two clips.

22. An orthodontic appliance according to claim 13 wherein the clip has an overall, generally "C"-shaped configuration.

23. An orthodontic appliance according to claim 13 wherein the clip includes a first section, a second section and a third section interconnecting the first section and the second section, and wherein the third section extends at an angle other than 90 degrees relative to the direction of extension of the first section and the second section.

* * * * *